(12) United States Patent
Komachi

(10) Patent No.: US 6,408,889 B1
(45) Date of Patent: Jun. 25, 2002

(54) BENDABLE TUBE AND METHOD FOR MANUFACTURING THE SAME

(75) Inventor: Yuichi Komachi, Akishima (JP)

(73) Assignee: Machida Endoscope Co., Ltd. (JP)

( * ) Notice: Subject to any disclaimer, the term of this patent is extended or adjusted under 35 U.S.C. 154(b) by 0 days.

(21) Appl. No.: 09/669,110

(22) Filed: Sep. 25, 2000

(30) Foreign Application Priority Data

Oct. 8, 1999 (JP) .......................................... 11-288004

(51) Int. Cl.$^7$ ................................................ F16L 11/18
(52) U.S. Cl. ...................... 138/120; 138/155; 600/141; 600/142; 29/432; 29/522.1
(58) Field of Search ................................ 138/119, 120, 138/155; 600/141, 142; 29/432, 437, 510, 522.1

(56) References Cited

U.S. PATENT DOCUMENTS

| | | | | |
|---|---|---|---|---|
| 1,630,588 A | * | 5/1927 | Sperry | 138/120 |
| 3,739,770 A | | 6/1973 | Mori | |
| 4,108,211 A | * | 8/1978 | Tanaka | 138/120 |
| 4,716,604 A | * | 1/1988 | Watkins | 138/155 |
| 4,834,069 A | | 5/1989 | Umeda | |
| 5,178,129 A | * | 1/1993 | Chikama et al. | 138/120 |
| 5,271,382 A | * | 12/1993 | Chikama | 138/120 |
| 5,839,476 A | * | 11/1998 | Blase | 138/120 |
| 5,928,136 A | * | 7/1999 | Barry | 600/142 |

FOREIGN PATENT DOCUMENTS

| | | |
|---|---|---|
| DE | 21 50 595 A | 4/1972 |
| EP | 0 439 931 A | 8/1989 |
| JP | 02 236038 A | 9/1990 |
| JP | 2619949 | 9/1997 |

* cited by examiner

*Primary Examiner*—James Hook
(74) *Attorney, Agent, or Firm*—Eugene Stephens & Associates

(57) ABSTRACT

A bendable tube used for an endoscope or the like, includes a plurality of joint pieces 11 arranged in a row. Each of the joint pieces is provided at one end portion thereof with a pair of first connecting portions 12 and at the other end portion with a pair of second connecting portions 13. The first connecting portions 12 are projected in a center axis direction of the joint piece and arranged 180 degrees away from each other in a peripheral direction, and the second connecting portions 13 are projected in the opposite direction to the first connecting portions 12 and arranged 180 degrees away from each other in the peripheral direction. The first connecting portion 12 is formed with a through-hole 12a (retaining portion) and the second connecting portion 13 is formed with a protrusion 13a. The first and second connecting portions 12, 13 of the adjacent joint pieces 11 are connected together only by fitting engagement between the protrusion 13a and the through-hole 12a. A rivet is not used for this connection. The first and second connecting portions are able to rotate relative to each other due to rubbing relation between an annular inner periphery of the through-hole 12a and an outer periphery of the protrusion 13a.

2 Claims, 6 Drawing Sheets

BENDABLE TUBE AND METHOD FOR MANUFACTURING THE SAME

BACKGROUND OF THE INVENTION

This invention relates to a bendable tube for an endoscope, a catheter or the like, and a method for manufacturing the same.

In general, an endoscope includes a main body, an elongated insertion portion extending from the main body and a bendable tube disposed at a distal end of the insertion portion and remote controlled from the main body. The bendable tube includes a plurality of tubular joint pieces arranged in a row. Each joint piece is provided at one end portion thereof with one pair of first connecting portions and at the other end portion with one pair of second connecting portions. The first connecting portions are projected in a center axis direction of the joint piece and arranged 180 degrees away from each other in a peripheral direction and the second connecting portions are projected in the opposite direction to the first connecting portions and arranged 180 degrees away from each other in the peripheral direction. The first and second connecting portions of the adjacent joint pieces are overlapped with each other in a radical direction and rotatably connected together by a rivet (shaft member). Owing to this arrangement, the entire bendable tube can be bent.

In recent years, a thinner design of a bendable tube has been demanded. In line with this demand, the joint piece is also demanded to be miniaturized in diameter. For example, it is demanded that the joint piece is designed to have a diameter of about 1 to 2 mm or even smaller. However, in the above-mentioned general construction, the more the diameter of the joint piece is designed to be small, the more the connecting work using a rivet becomes difficult to perform. Thus, in a bendable tube disclosed in Japanese Patent Publication No. 2,619,949, a first connecting portion is formed with a through-hole and a second connecting portion is provided with a protruding element projecting in an axial direction of a joint piece. The protruding element is inserted into the through-hole and bent 180 degrees. By this, the adjacent joint pieces are connected together without a need of a rivet.

In the bendable tube disclosed in the above Publication, a thinner design is made possible because there is no need of a provision of a rivet, but there is involved such a problem that the bending operation is difficult to make because the frictional resistance is large between the protruding element and the through-hole.

SUMMARY OF THE INVENTION

It is an object of the present invention to provide a bendable tube in which adjacent joint pieces are connected without a need of a rivet thereby enabling to make a thinner design of the bendable tube and in which a smooth bending operation can be obtained.

It is another object of the present invention to provide a method for easily manufacturing a bendable tube having a thinner design in which a bending operation can be made smoothly without a need of a rivet.

A bendable tube according to the present invention includes, as a basic constitution, a plurality of tubular joint pieces arranged in a row. Each of the joint pieces is provided at one end portion thereof with a pair of first connecting portions and at the other end portion with a pair of second connecting portions. The first connecting portions are projected in a center axis direction of the joint piece and arranged 180 degrees away from each other in a peripheral direction and the second connecting portions are projected in the opposite direction to the first connecting portions and arranged 180 degrees away from each other in the peripheral direction. Moreover, in the bendable tube of the present invention, each of the first connecting portions is formed with a retaining portion having an inner periphery at least a part of which is arcuate and each of the second connecting portions is formed with a protrusion. The first and second connecting portions are connected together only by fitting engagement between the protrusion and the retaining portion. The first and second connecting portions are able to rotate relative to each other due to rubbing relation between an inner periphery of the retaining portion and an outer periphery of the protrusion. As a result, a rivet as a connecting means can be eliminated. Moreover, the friction between the first and second connecting portions can be made comparatively small and the bendable tube can easily be bent.

Preferably, the first connecting portion is arranged radially inside and the second connecting portion is arranged radially outside, the protrusion being projected radially inward from the second connecting portion so as to be fitted into the retaining portion of the first connecting portion. This constitution is suited to be employed when the protrusion is formed by pressing.

Preferably, at least a part of the outer periphery of the protrusion is arcuate. The rubbing relation between the outer periphery of the protrusion and the arcuate inner periphery of the retaining portion ensures a smooth relative rotation of the first ::and second connecting portions.

Preferably, the inner periphery of the retaining portion is a perfect circle. This feature ensures a more smooth relative rotation between the first and second connecting members.

The retaining portion may be composed of a circular through-hole. This through-hole allows the insertion of the protrusion. In the case where the protrusion includes a cylindrical peripheral wall, a smooth relative rotation between the first and second connecting portions is ensured. By providing an annular engagement portion engageable with a peripheral edge of the through-hole at a distal end of the peripheral wall of the protrusion, a reliable connection between the first and second connecting portions can be obtained.

The retaining portion and the protrusion may have a cylindrical peripheral wall and a bottom wall, which walls are rubbed with each other.

In a first embodiment of a method for manufacturing a bendable tube according to the present invention, a first connecting portion of a joint piece is preliminarily formed with a through-hole. In the joint pieces to be placed adjacent to each other, the second connecting portion of one of the adjacent joint pieces is radially externally overlapped with the first connecting portion of the other adjacent joint piece and the second connecting portion is pressed from outside, thereby forming a protrusion projecting inward in a radial direction and fitting into the through-hole. The joint pieces are rotatably connected together only by this fitting engagement between the protrusion and the through-hole. In this way, a very thin bendable tube can be manufactured easily, at a low cost and in a short time.

In a second embodiment of a method for manufacturing a bendable tube according to the present invention, in the joint pieces to be placed adjacent to each other, the second connecting portion of one of the adjacent joint pieces is radially externally overlapped with the first connecting portion of the other adjacent joint piece and such overlapped first and second connecting portions are pressed altogether from outside, thereby forming a circular recess in an outer peripheral surface of the first connecting portion and a circular protrusion on the second connecting portion simultaneously, the circular protrusion being projected inward in a radial direction and fitted into the retaining portion, the joint pieces being rotatably connected together only by this fitting engagement between the protrusion and the recess. In this way, a very thin bendable tube can be manufactured easily, at a low cost and in a short time.

DETAILED DESCRIPTION OF THE INVENTION

Embodiments of the present invention will now be described with reference to the drawings.

Figure 5:
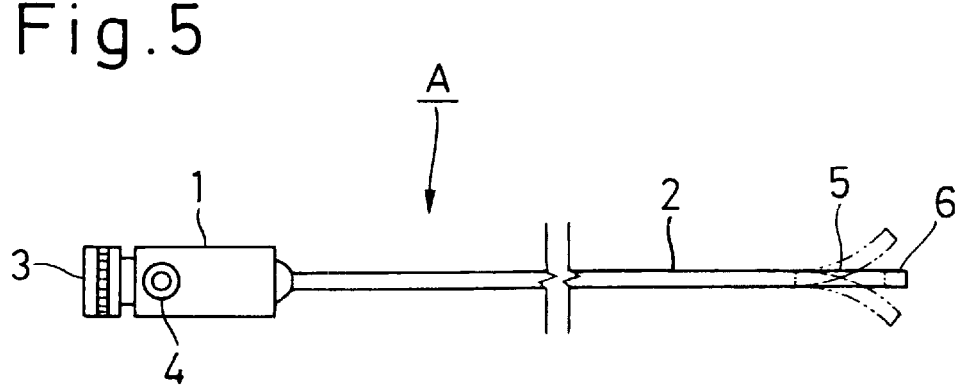
FIG. 5 is a side view showing an overall endoscope.

First, an endoscope A, in which a bendable tube is used, will be described roughly with reference to FIG. 5. The endoscope A includes a main body 1 and an insertion portion 2 extending from the main body 1 and allowed to be inserted into a patient's body. The main body 1 is provided with an ocular portion 3 and a handle 4. The insertion portion 2 is formed to be flexible and provided at a distal end thereof with a bending portion 5 which is remote controlled by the handle 4. The bending portion 5 is provided at a distal end thereof with a tip 6. The tip 6 is provided with an observation window (not shown). An image of an interior of the patient's body is made incident to this observation window and transmitted to the ocular portion 3 through a flux of optical fibers inserted into the insertion portion 2 and the main body 1.

Figure 1:
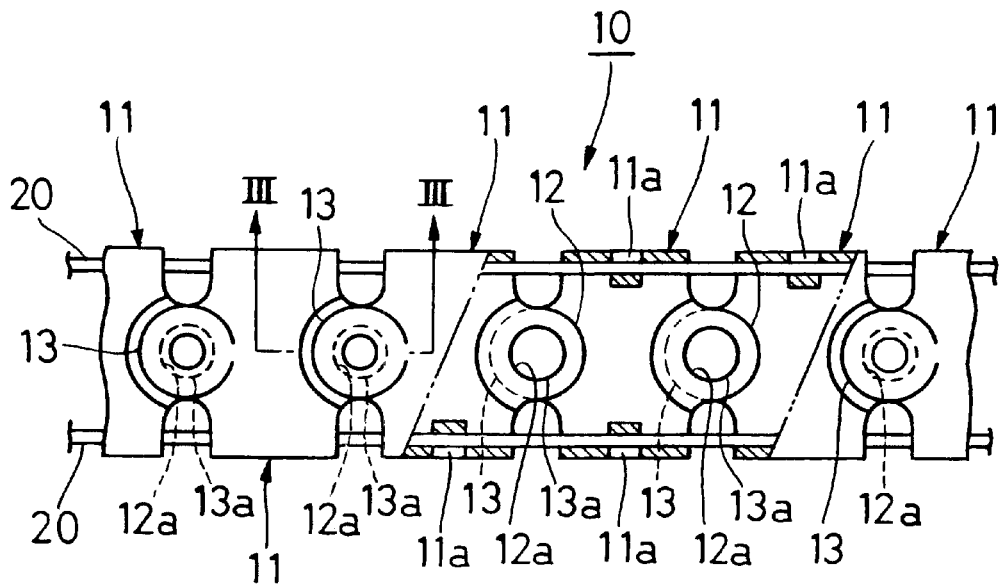
FIG. 1 is a side view, partly in section, showing a bendable tube of an endoscope according to a first embodiment of the present invention.

The bending portion 5 contains therein a bendable tube 10 shown in FIG. 1. The bendable tube 10 includes a plurality of tubular joint pieces 11 which are made of metal. Those joint pieces 11 are arranged in a row. End portions of the adjacent joint pieces 11 are rotatably connected together. The insertion portion 2 and the bending portion 5 are very thin. Each joint piece 11 is about 1 to 2 mm in diameter. Because this connecting construction is a subject matter of the present invention, it will be described in detail later.

Each joint piece 11 is provided at a center thereof in a center axis C direction with one pair of wire insertion holes 11a or wire insertion portions which are arranged 180 degrees away from each other in a peripheral direction. One pair of control wires 20 are inserted into those wire insertion holes 11a, respectively. Although not shown, one end of each control wire 20 is fixed either to that joint piece 11 which is disposed at the foremost end, or the tip 6, and the other end is connected to the handle 4. As indicated by an imaginary line in FIG. 5, when the handle 4 is rotationally operated in one direction, one of the control wires 20 is pulled and when it is rotationally operated in the opposite direction, the other control wire 20 is pulled. By this, the bendable tube 10 and hence the bending portion 5 are selectively bent in two directions.

A connecting construction between the end portions of the adjacent joint pieces 11 will now be described.

Figure 2:
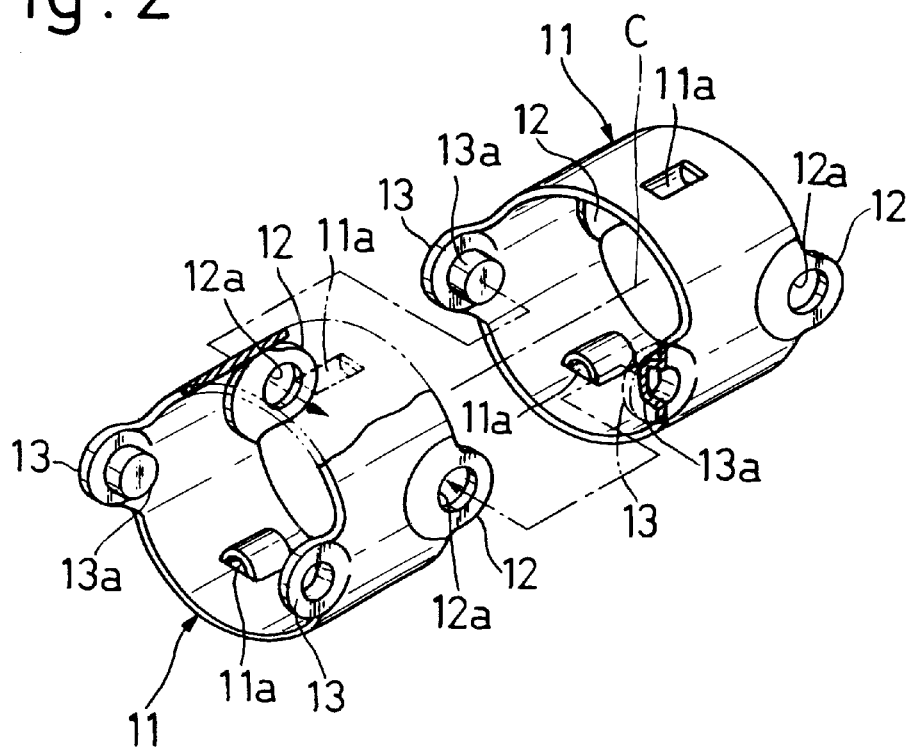
FIG. 2 is an exploded perspective view showing adjacent two joint pieces in the above bendable tube.
Figure 3:
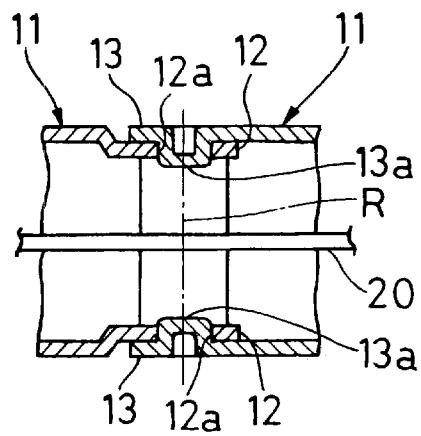
FIG. 3 is a sectional view taken on line III—III of FIG. 1.

As shown in FIGS. 1 to 3, each joint piece 11 is provided at one end portion thereof with one pair of first connecting portions 12 which are arranged 180 degrees away from each other in the peripheral direction. The first connecting portions 12 are offset 90 degrees from the wire insertion hole 11a in the peripheral direction. Each first connecting portion 12 exhibits a flat disk-like configuration and about a half part of the first connecting portion 12 projects in the center axis C direction of the joint piece 11. A circular through-hole 12a (retaining portion having a circular inner periphery) is formed in the center of the first connecting portion 12.

Similarly, each joint piece 11 is provided at the other end portion with one pair of second connecting portions 13 which are arranged 180 degrees away from each other in the peripheral direction. The second connecting portion 13 is disposed at a location which is in alignment with the first connecting portion 12 along the center axis C direction of the joint piece 11. The second connecting portion 13 exhibits a flat disk-like configuration and about a half part of the second connecting portion 13 projects in the opposite direction to the first connecting portion 12. A radially inwardly projecting protrusion 13a is disposed at the center of the second connecting portion 13. This protrusion 13a includes a cylindrical peripheral wall and a bottom wall for closing a radially inner end of the peripheral wall.

In the adjacent two joint pieces 11, the first connecting portion 12 of one of the joint piece 11 is brought into coincident with the second connecting portion 13 of the other joint piece 11 in the peripheral direction, and the second connecting portion 13 is radially externally overlapped with the first connecting portion 12. Then, the protrusion 13a of the second connecting portion 13 is fitted into the through-hole 12a of the first connecting portion 12. The first and second connecting portions 12, 13 are connected together only by fitting engagement between the through-hole 12a and the protrusion 13a and there is no need of a provision of a rivet (shaft member). Therefore, even if the joint pieces 11 are very small in diameter, they can be connected to each other easily. Thus, the bendable tube 10 can be designed to be very thin. Moreover, due to rubbing relation between the circular inner peripheral of the through-hole 12a and the circular outer periphery of the protrusion 13a, the first and second connecting portions 12, 13 can rotate about a radially extending rotation axis R smoothly and stably and thus, the adjacent joint pieces 11 can rotate relative to each other smoothly. Accordingly, the bending tube 10 can be bent smoothly by remote control of the handle 4.

Figure 4:
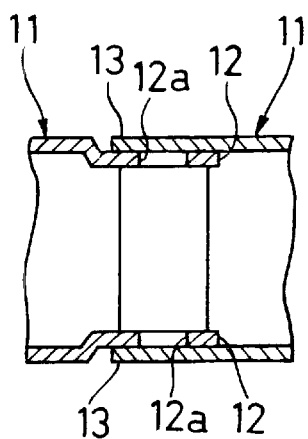
FIG. 4 is a sectional view showing an initial stage of the process for connecting the adjacent two joint pieces.

A process for manufacturing the bendable tube 10 will now be described with reference to FIGS. 3 and 4. A plurality of joint pieces 11 each having the first connecting portions 12 with a through-hole 12a preliminarily formed therein and the second connecting portions 13 are prepared. Then, as shown in FIG. 4, the first and second connecting portions 12, 13 of the adjacent two joint pieces 11 are radially overlapped with each other. Then, the protrusions 13a, as shown in FIG. 3, are shaped by pressing the second connecting portions 13 in the radial direction from outside and at the same time, the protrusions 13a are fitted into the through-holes 12a. Since the first and second connecting portions 12, 13 are connected together simultaneous with the shaping of protrusions 13a, the number of the connecting processes can be. reduced. The connecting work may be sequentially performed first with the joint piece 11 located nearest to the basal end towards the distal end, or vice versa. After a predetermined number of joint pieces 11 are connected together, the control wire 20 is inserted into the wire insertion hole 11a. It is also accepted that after the control wire 20 is preliminarily inserted into the joint piece 11 to be newly connected, the first and second connecting portions 12, 13 are connected together.

Figure 6:
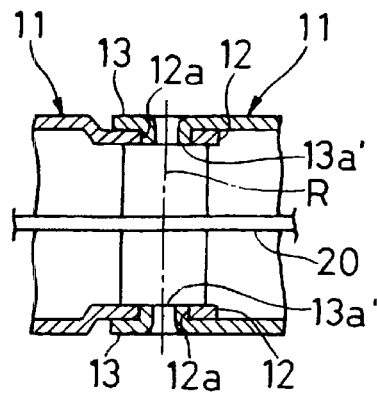
FIG. 6 is a sectional view of an essential portion of a bendable tube according to a second embodiment of the present invention.

Other embodiments of the present invention will now be described. In those embodiments, like component parts of the first embodiment are denoted by like reference numerals so that description thereof can be simplified. FIG. 6 shows a second embodiment of the present invention. In this embodiment, each of protrusions 13a' has a cylindrical peripheral wall but it has no bottom wall. A radially inner end portion of the protrusion 13a' is open.

Figure 7:
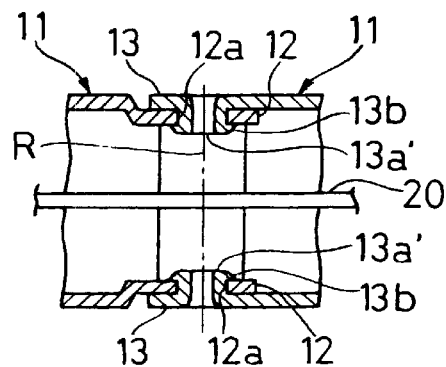
FIG. 7 is a sectional view of an essential portion of a bendable tube according to a third embodiment of the present invention.

FIG. 7 shows a third embodiment of the present invention. This embodiment is a modified embodiment of the second embodiment. An annular engagement portion 13b engageable with an edge of a through-hole 12a is formed in an inner end portion of a protrusion 13a'. By this, first and second connecting portions 12, 13 of adjacent joint pieces 11 can positively be prevented from being disconnected.

Figure 8:
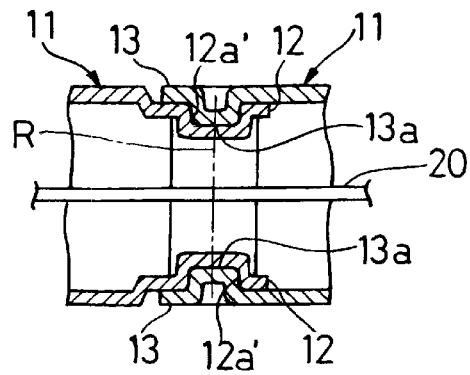
FIG. 8 is a sectional view of an essential portion of a bendable tube according to a fourth embodiment of the present invention.

FIG. 8 shows a fourth embodiment of the present invention. In this embodiment, a first connecting portion 12 is formed with a recess 12a' (retaining portion) instead of the through-hole 12a of the first to third embodiments. The recess 12a' is recessed radially inward. It includes a cylindrical peripheral wall and a bottom wall for closing a radially inner end of the peripheral wall. A protrusion 13a is fitted into the recess 12a'. Rubbing relation between a cylindrical outer periphery of the protrusion 13a and a cylindrical inner periphery of the recess 12a' enables the first and second connecting portions 12, 13 to rotate relative to each other.

Figure 9:
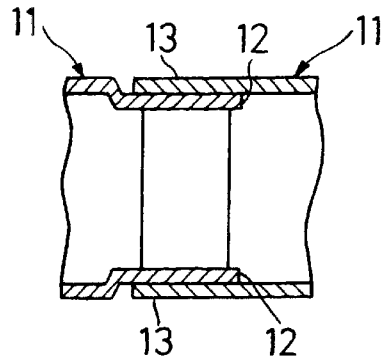
FIG. 9 is a sectional view showing an initial stage of the process for connecting adjacent two joint pieces in the bendable tube according to the fourth embodiment.

A process for manufacturing the bending tube of the above-mentioned fourth embodiment will now be described with reference to FIGS. 8 and 9. A plurality of joint pieces 11 having the first and second connecting portions 12, 13 are prepared. By pressing the overlapped first and second connecting portions 12, 13 from outside as shown in FIG. 9, the recesses 12a' and the protrusions 13a are simultaneously shaped and fitted to each other as shown in FIG. 8. By connecting a predetermined number of joint pieces 11 together, a bendable tube is formed. In this fourth embodiment, the time for manufacturing the bendable tube 10 can further be shortened.

In fifth to eighth embodiments shown in FIGS. 10 to 13, the overlapping manner of the first and second connecting portions 12, 13 are reversed to that of the first to fourth embodiment. That is to say, the first and second connecting portions 12, 13 are overlapped with each other such that the first connecting portion 12 is located outside and the second connecting portion 13 is located inside along the radial direction of the bendable tube 10. Those embodiments will be described individually hereinafter.

Figure 10:
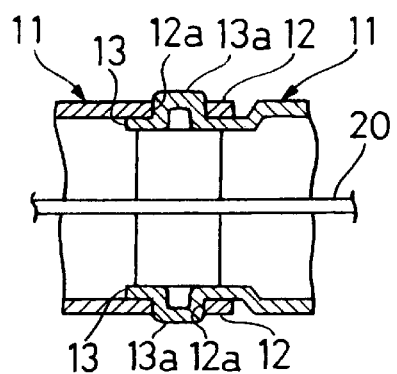
FIG. 10 is a sectional view of an essential portion of a bendable tube according to a fifth embodiment of the present invention.

In the fifth embodiment shown in FIG. 10, protrusions 13a whose distal ends are closed are projected radially outward from the second connecting portion 13 and fitted into through-holes 12a of first connecting portions 12.

Figure 11:
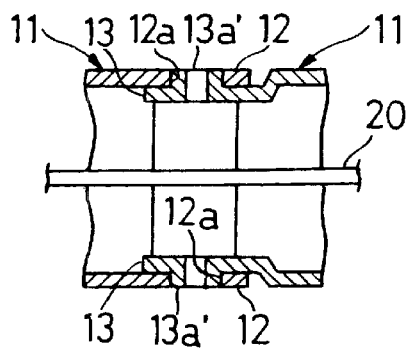
FIG. 11 is a sectional view of an essential portion of a bendable tube according to a sixth embodiment of the present invention.

In the sixth embodiment shown in FIG. 11, protrusion 13a' whose distal ends are open are projected radially outward and fitted into through-holes 12a.

Figure 12:
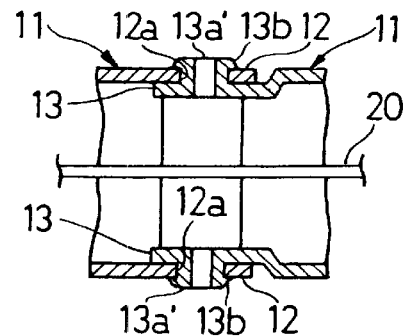
FIG. 12 is a sectional view of an essential portion of a bendable tube according to a seventh embodiment of the present invention.

In the seventh embodiment shown in FIG. 12, an annular engagement portion 13b is disposed at an outer end portion of each of radially outwardly projected protrusions 13a'. This engagement portion 13b is engaged with an edge of a through-hole 12a.

Figure 13:
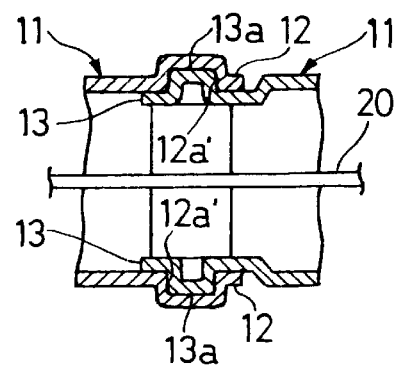
FIG. 13 is a sectional view of an essential portion of a bendable tube according to an eighth embodiment of the present invention.

In the eighth embodiment shown in FIG. 13, recesses 12a', which are recessed radially outward, are formed in the first connecting portion 12 and radially outwardly projecting protrusions 13a of the second connecting portion 13 are fitted into the recesses 12a'.

In the embodiments shown in FIGS. 10 to 13, the joint pieces 11 can be connected together by pressing as well.

Figure 14:
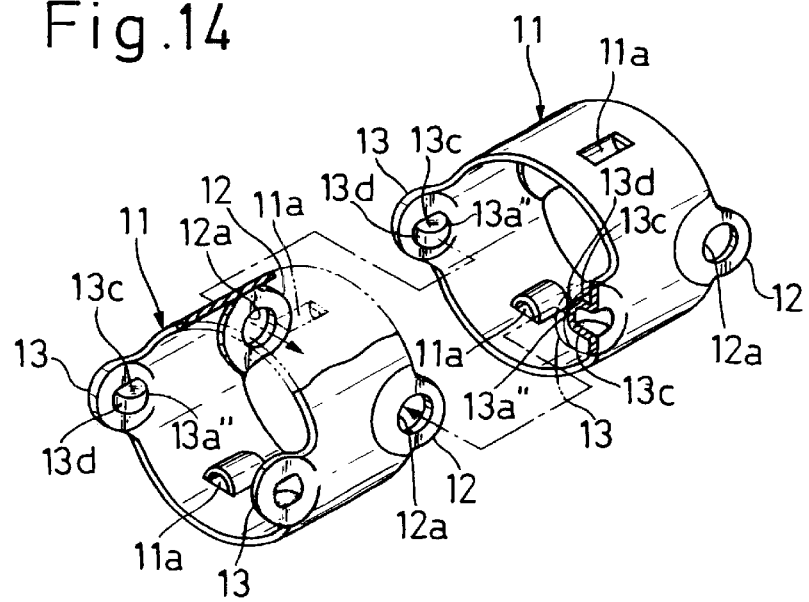
FIG. 14 is an exploded perspective view showing adjacent two joint pieces in a bendable tube according to a ninth embodiment of the present invention.

FIG. 14 shows a ninth embodiment of the present invention. In this embodiment, an outer periphery of each protrusion 13a" formed on a second connecting portion 13 includes a pair of semi-circular flat walls 13c and a bent wall 13d formed between the flat surfaces 13c. Opposite end portions of the bent wall 13d draws, when viewed in a radial direction, a circular arc pattern having a radius of curvature generally equal to that of a through-hole 12a of a first connecting portion 12. Rubbing engagement between outer peripheries of the opposite end portions of the bent wall 13d and the inner periphery of the through hole 12a enable the first and second connecting portions 12, 13 to rotate relative to each other. Thus, adjacent joint pieces 11 can rotate relative to each other smoothly.

Figure 15:
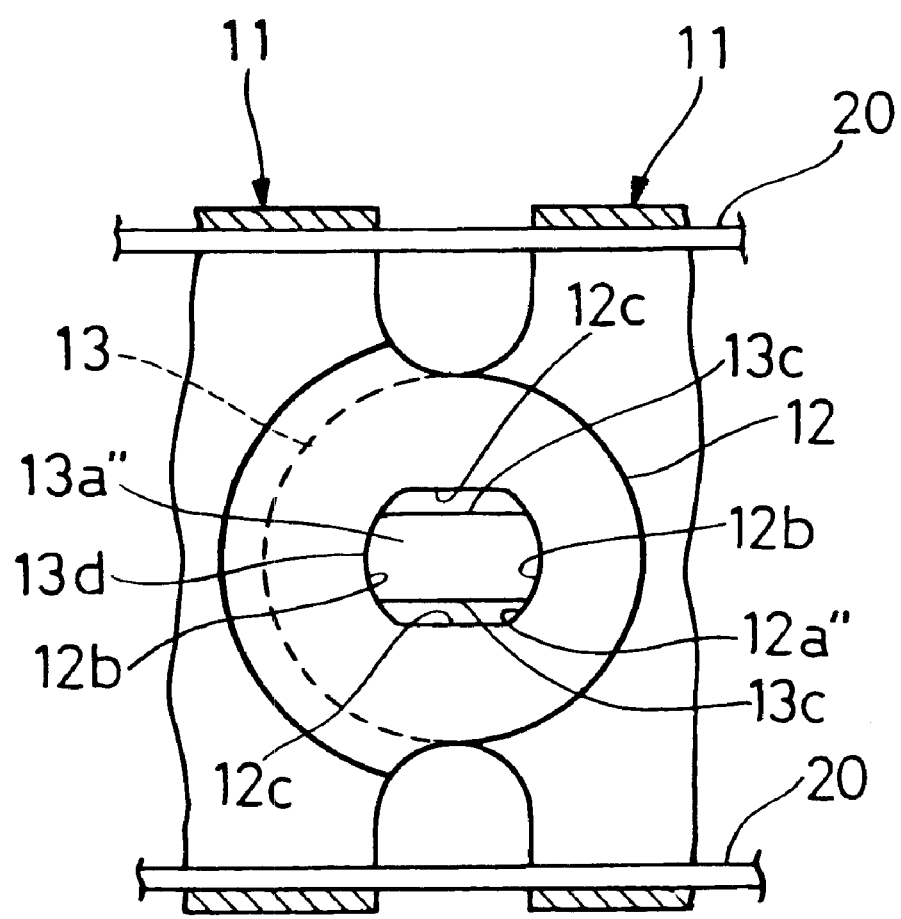
FIG. 15 is a sectional view of an essential portion of a bendable tube according to a tenth embodiment of the present invention.

FIG. 15 shows a tenth embodiment of the present invention. This embodiment is a modified embodiment of the above-mentioned ninth embodiment. An inner periphery of a through-hole 12a" of each first connecting portion 12 includes a pair of arcuate portions 12b which are rubbed with round portions 13d of the protrusions 13a" and a pair of linear portions 12c disposed between the arcuate portions 12b. Although the arcuate portion 12b of the through-bole 12 and the circular arcs of the outer peripheries of the opposite end portions of the bent wall 13d are generally equal in radius of curvature, the arcuate portion 12b is longer than the outer peripheries of the opposite end portions of the bent wall 13d. Owing to this feature, the first and second connecting portions 12, 13 can rotate relative to each other.

The present invention should not be limited to the above embodiments. Instead, many other changes and modifications can be made.

For example, the present invention can also be applied to a bendable tube which can be bent in four directions. In that case, the first connecting portion and the second connecting portion are offset 90 degrees in the peripheral direction.

It is also accepted that the first connecting portion 12 is preliminarily formed with through-holes 12a, 12a" or a recess 12a' and the second connecting portion 13 is preliminarily formed with protrusions 13a, 13a', 13a", so that the protrusions 13a, 13a', 13a" are fitted into the through-holes 12a, 12a" or the recess 12'.

The bendable tube of the present invention can be applied not only to an endoscope but also to a catheter.

What is claimed is:

1. A method for manufacturing a bendable tube for an endoscope, a catheter, or the like having a plurality of joint pieces which are made of metal and arranged in a row, said method comprising the steps of:

(a) preparing said joint pieces each of which has a tubular configuration, each of said joint pieces being provided at one end portion thereof with a pair of first connecting portions and at the other end portion with a pair of second connecting portions, said first connecting portions being projected in a center axis direction of said joint piece and arranged 180 degrees away from each other in a peripheral direction, said second connecting portions being projected in the opposite direction to said first connecting portions and arranged 180 degrees away from each other in the peripheral direction, said first connecting portions each being formed with a through-hole;

(b) in said joint pieces to be placed adjacent to each other, radially externally overlapping said second connecting portion of one of said adjacent joint pieces with said first connecting portion of the other adjacent joint piece; and (c) in the overlapped condition of said first and second connecting portions, pressing said second connecting portion from outside, thereby forming a protrusion projected inward in a radial direction and simultaneously fitting said protrusion into said through-hole, said joint pieces being rotatably connected together only by this fitting engagement between said protrusion and said through-hole.

2. A method for manufacturing a bendable tube for an endoscope, a catheter, or the like having a plurality of joint pieces which are made of metal and arranged in a row, said method comprising the steps of:

(a) preparing said joint pieces each of which has a tubular configuration, each of said joint pieces being provided at one end portion thereof with a pair of first connecting portions and at the other end portion with a pair of second connecting portions, said first connecting portions being projected in a center axis direction of said joint piece and arranged 180 degrees away from each other in a peripheral direction, said second connecting portions being projected in the opposite direction to said first connecting portions and arranged 180 degrees away from each other in the peripheral direction;

(b) in said joint pieces to be placed adjacent to each other, radially externally overlapping said second connecting portion of one of said adjacent joint pieces with said first connecting portion of the other adjacent joint piece; and (c) pressing such overlapped first and second connecting portions altogether from outside, thereby forming a circular recess in an outer peripheral surface of said first connecting portion and a circular protrusion projected inward in a radial direction on said second connecting portion, and simultaneously fitting said protrusion into said recess, said joint pieces being rotatably connected together only by this fitting engagement between said protrusion and said recess.

* * * * *